United States Patent [19]

Bentzen et al.

[11] 4,309,364
[45] Jan. 5, 1982

[54] DIPHOSPHONATES

[75] Inventors: Craig L. Bentzen, Onex; Lan N. Mong, Nyon; Eric Niesor, Gland, all of Switzerland

[73] Assignee: Symphar S.A., Le Lignon, Switzerland

[21] Appl. No.: 114,423

[22] Filed: Jan. 22, 1980

[30] Foreign Application Priority Data

Feb. 13, 1979 [GB] United Kingdom ............... 4992/79
Sep. 25, 1979 [GB] United Kingdom ............. 33157/79

[51] Int. Cl.³ .......................... C07F 9/11; C07F 9/40; A61K 31/66
[52] U.S. Cl. ................................ 260/931; 260/932; 260/502.4 P; 424/204
[58] Field of Search ................................ 260/931, 932

[56] References Cited

U.S. PATENT DOCUMENTS

| | | | |
|---|---|---|---|
| 2,848,475 | 8/1958 | Schmidt | 260/932 |
| 3,299,123 | 1/1967 | Fitch et al. | 260/932 |
| 3,463,835 | 8/1969 | Budnick | 260/932 |
| 3,471,406 | 10/1969 | Budnick | 260/932 |
| 4,067,971 | 1/1978 | Francis et al. | 424/204 |
| 4,113,861 | 9/1978 | Fleisch et al. | 424/204 |
| 4,137,309 | 1/1979 | Van Duzee | 424/204 |

FOREIGN PATENT DOCUMENTS

| | | | |
|---|---|---|---|
| 1394386 | 2/1965 | France | 260/932 |
| 8441M | 6/1971 | France | 424/202 |

OTHER PUBLICATIONS

Puddvik et al., "Index Chemicus," vol. 28, (1968), #89485.

Nicholson et al., "J. Org. Chem.", vol. 36, No. 24, (1971), pp. 3843-3845.

Primary Examiner—Anton H. Sutto
Attorney, Agent, or Firm—Young & Thompson

[57] ABSTRACT

This invention relates to new diphosphonate compounds of formula (I)

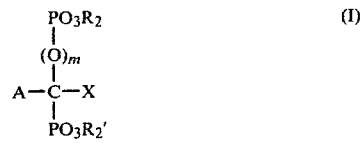

where X is H, OH,

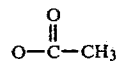

or $NH_2$; R and R' identical or different are H, $CH_3$ or $C_2H_5$; m is zero or 1; and A is selected from the group comprising $(CH_3)_3C-$, $Y-C_6H_4-$, $Y-C_6H_4-O-C(CH_3)_2-$, $Y-C_6H_4-C(CH_3)_2-$, $Y-C_6H_4-CO-C_6H_4-$, $Y-C_6H_4-(CH_2)_n-$ and $Y-C_6H_4-O-(CH_2)_n-$, where n is an integer from 1 to 6 and Y is H, $CH_3$, $OCH_3$ or Cl. These compounds possess remarkable activity as hypoglycemic and/or antiatherogenic agents, and are usable in pharmaceutical compositions to alter lipoprotein profiles in favor of high density lipoproteins and to clear cholesterol from various tissues.

11 Claims, No Drawings

DIPHOSPHONATES

The present invention related to diphosphonate derivatives, and more particularly to phenylalkyl- and phenoxyalkyl-diphosphonates and hydroxydiphosphonates, as well as antiatherogenic preparations containing said compounds for the treatment of human cardiovascular diseases.

Over the past few years, coronary heart prevention studies have been performed with common hypolipidemic agents such as clofibrate. More recently, the results of these studies have left the therapeutic effectiveness of these compounds in question (see for example New Engl. J. Med. 296, 1185-1190, 1970; Atherosclerosis Rev. 2, 113-153, 1977; The Lancet 8100, 1131-1132, 1978; and Brit. Med. J. 6152, 1585, 1978).

It is now desirable to make use of compounds which have a rapid and effective activity for decreasing cholesterol content directly in the tissues and not only in blood as it is the case of most common hypolipidemic agents.

Therefore, the present inventors have undertaken investigations on diphosphono compounds and have found that diphosphonates represented by general formula (I) possess a remarkable activity as antiatherogenic agents, as well as the ability to alter lipoprotein profiles in favour of high density lipoproteins and to directly clear cholesterol from various tissues.

This ability to remove cholesterol from tissues gives to these compounds (I) the potential of being used in diseases triggered by, or resulting from, abnormal cholesterol synthesis, metabolism and deposition. For example, cardiovascular diseases in general which are associated with cholesterol deposition in arterial walls (Atheromas), familial hypercholesterolemia and cholesterol deposition in subcutaneous tissues (Xanthomatosis), gallstones (cholesterol precipitated), cancer tissues in which cholesterol metabolism is impaired, and thrombosis due to cholesterol rich-hypersensitive platelets (Shattil, S. J. et al The Journal of Clinical Investigation 55, 636-643, 1975), etc.

Since cholesterol is the precursor for steroid hormones (male and female sex hormones and for corticosteroids), abnormal synthesis of these hormones might be regulated by the use of such compounds. The possible uses of phosphonates in the fields described above are under investigation. Some of these compounds of formula (I) further possess an activity as hypoglycemic agents.

$$\begin{array}{c} PO_3R_2 \\ | \\ (O)_m \\ | \\ A-C-X \\ | \\ PO_3R_2' \end{array} \quad (I)$$

In the above formula (I), X is H, OH, $$\begin{array}{c} O \\ \| \\ O-C-CH_3 \end{array}$$

or $NH_2$; R and R' identical or different are H, $CH_3$ or $C_2H_5$; m is zero or 1; and A is selected from the group comprising

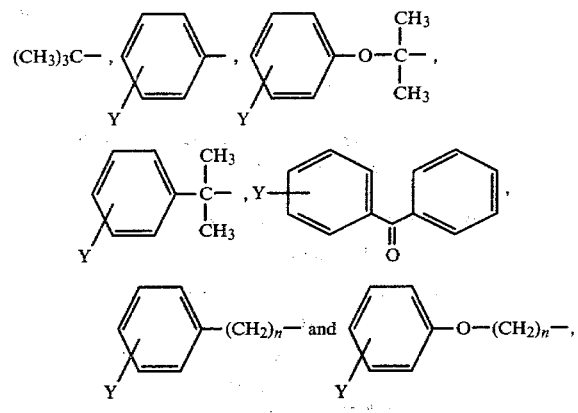

where n is an integer from 1 to 6 and Y is H, $CH_3$, $OCH_3$ or Cl.

The hydroxydiphosphonate compounds of formula (Ia), $$\begin{array}{c} PO_3R_2 \\ | \\ A-C-OH \\ | \\ PO_3R_2' \end{array} \quad (Ia)$$

where R, R' and A are as defined above, can be prepared according to the following scheme (with $R=R'=CH_3$ or $C_2H_5$):

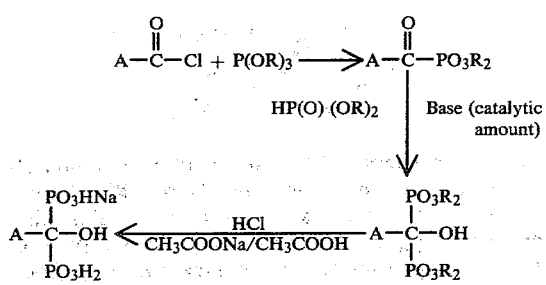

The phosphonophosphates of formula (Ib):

$$\begin{array}{c} PO_3R_2 \\ | \\ O \\ | \\ A-C-H \\ | \\ PO_3R_2' \end{array} \quad (Ib)$$

where R, R' and A are as defined above, can be prepared according to the following scheme (with $R=R'=CH_3$ or $C_2H_5$):

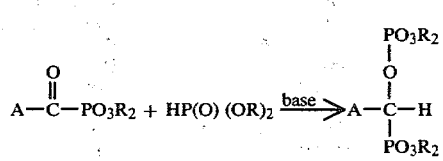

The diphosphonate compounds of formula (Ic),

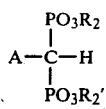

where R, R' and A are as defined can be prepared according to the following scheme:

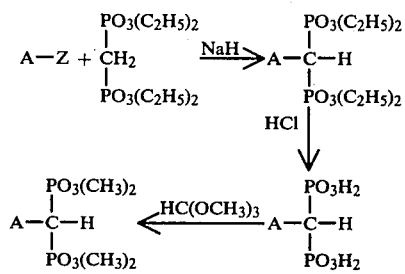

where Z is Br or Cl.

The present invention will be now further described by reference to the following Examples 1 to 7 directed to the preparation of some of the compounds of formula (I).

EXAMPLE 1

Tetramethyl-1 (p-chlorophenyl)methane 1-hydroxy 1,1-diphosphonate (Compound 4)

(Method adapted from D. A. Nicholson and H. Vaughn, Journal of Organic Chemistry 36, 3843, 1971).

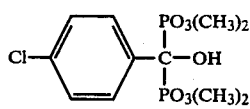

Dimethyl phosphite (4.40 g, 40 mmol) and di(n-butyl)amine (0.24 g, 2 mmol) were dissolved in 90 ml ether and the resulting solution was cooled to 0° C. Dimethyl p-chlorobenzoylphosphonate (9.96 g, 40 mmol) (prepared according to Journal of American Chemical Society 86, 3862, 1964) was added dropwise with rapid stirring. A white solid separated out almost immediately. The mixture was stirred for one hour at 0°, and filtration yielded 13.0 g (36 mmol) of the title compound.

Purification was done by dissolving the crude compound in acetone at room temperature and adding ether to crystallize it (acetone:ether ratio=3:1). 7,9 g (22 mmol) of white crystals were obtained, with a yield (pure compound) of 55%.

|          | yield (crude)        | = 90%          |
|----------|----------------------|----------------|
|          | mp                   | = 119-123° C.  |
| IR (KBr) | : 3260 cm$^{-1}$     | : OH           |
|          | 2880                 | : aliphatic C—H |
|          | 1500                 | : aromatic C—C |
|          | 1280 + 1240          | : P=O          |
|          | 1060                 | : P—O—C        |
| MS : m/e = | 360 (M + 2)$^+$    | : 17%          |
|          | 358 (M)$^+$          | : 52%          |
|          | 251 (M + 2-PO$_3$Me$_2$)$^+$ | : 33%  |
|          | 249 (M—PO$_3$Me$_2$)$^+$ | : 100%     |

NMR (CDCl$_3$):

δ=7.90–7.20 (multiplet, 4H): phenyl group.
4.50–4.20 (triplet, 1H, J=7 Hz): H from hydroxyl group removed through exchange with deuterium oxide.
3.90–3.50 (multiplet, 12H): H from methyl groups.
Analysis: C$_{11}$H$_{17}$ClO$_7$P$_2$;
Calculated: C 36.84, H 4.78, P 17.27%; Found: C 36.81, H 4.78, P 17.26%.

As verification of its structure, compound 4 was transformed into the corresponding hydroxydiphosphonic acid, mono sodium salt (compound 10), as follows:

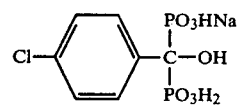

A mixture of 3.59 g (10 mmol) of compound 4 and 15 g of 37% hydrochloric acid was refluxed for 3 hours. The evaporation of HCl and H$_2$O left 3.2 g (10 mmol) of white solid.

mp: 192°–194° C. (crude)
yield: 100% (crude).

For purification purpose, hydroxy (p-chlorophenyl)-methylenediphosphonic acid was transformed into its mono-sodium salt, according to the following purification method adapted from P. F. Pflaumer and J. P. Filcik, Chemical Abstracts 72, 55656k, 1970:

The solid obtained as described above was dissolved in a mixture of 4.8 g (80 mmol) of acetic acid and 0.7 g (39 mmol) of water at 95°. Sodium acetate-trihydrate (1.36 g, 10 mmol) was then added gradually. A voluminous precipitate appeared almost instantly. It was filtrated and washed copiously with ether until the smell of acetic acid disappeared. The rinsed precipitate was recrystallized in an ethanol:water (20:80) mixture to give 1.94 g (6 mmol) of white powder of 1-hydroxy 1(p-chlorophenyl)methyl 1,1-diphosphonic acid, mono-sodium salt.

yield: 60%.

EXAMPLE 2

Tetramethyl 2,2-dimethyl 2(p-chlorophenoxy) ethane 1-hydroxy 1,1-diphosphonate (Compound 5)

(Method from K. D. Berlin et al, Journal of Organic Chemistry 30, 1265, 1965, and D. A. Nicholson and H. Vaughn, Journal of Organic Chemistry 36, 3843, 1971).

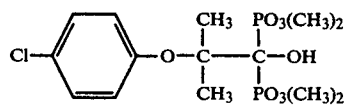

p-Chlorophenoxyisobutyryl chloride was first prepared by alkaline hydrolysis of ethyl p-chlorophenoxyisobutyrate and refluxing the acid obtained in thionyl chloride, in following the standard procedures.

An amount of 10.6 g (86 mmol) of trimethyl phosphite was added dropwise to 20.0 g (86 mmol) of p-chlorophenoxyisobutyryl chloride cooled to 0° C. As varification of the reaction, evolution of methyl chloride could be observed. Distillation under reduced pressure gave 19.0 g (62 mmol) of dimethyl p-chlorophenoxyisobutyrylphosphonate as an almost colorless oil.

| bp | = 115-118°/5.10$^{-2}$ Torr | |
|---|---|---|
| yield | = 72% | |
| IR(film) | : 3000 cm$^{-1}$ | : aliphatic C—H |
| | 1740 | : C=O |
| | 1500 | : aromatic C—C |
| | 1250 | : P=O |
| | 1050 | : P—O—C |
| | 830 | : 1,4-disubstituted phenyl |

Then a solution of 2.86 g (26 mmol) dimethyl phosphite and 0.18 g (1.4 mmol) di(n-butyl)amine in 65 ml ether was cooled to 0° C., and dimethyl p-chlorophenoxyisobutyrylphosphonate (7.97 g, 26 mmol) was introduced slowly with rapid stirring. A white solid began to form almost immediately. The reaction was left to stir at 0° C. for one hour, then the solid was separated by filtration. Recrystallization in benzene:hexane (60:40) gave 7.18 g (17.2 mmol) of white feathery crystals of the title compound i.e. tetramethyl 2,2-dimethyl 2(p-chlorophenoxy) ethane 1-hydroxy 1,1-diphosphonate.

| mp | = 137-139° C. | |
|---|---|---|
| yield | = 66% | |
| IR (KBr) | : 3360 cm$^{-1}$ | : OH |
| | 3000 | : aliphatic C—H |
| | 1500 | : aromatic C—C |
| | 1250 + 1220 | : P=O |
| | 1070 | : P—O—C |
| | 860 | : 1,4-disubstituted phenyl |

NMR (CDCL$_3$):

$\delta$ = 7.4–7.0 (multiplet, 4H): phenyl group.

4.0–3.70 (multiplet, 12H): H from methyl groups bound to the phosphonate moieties.

3.6–3.4 (hump, 1H): H from the hydroxyl group, removed through exchange with D$_2$O.

1.58 (singlet, 6H): H from the branched methyl groups.

Analysis: C$_{14}$H$_{23}$ClO$_8$P$_2$; Calculated: C 40.45 H 5.58 P 14.90%; Found: C 40.29 H 5.94 P 14.93%.

EXAMPLE 3

Tetramethyl 1[4(4'-chlorobenzoyl)-phenyl]methane 1-hydroxy 1,1-diphosphonate (Compound 6).

(Method adapted from D. A. Nicholson and H. Vaughn, Journal of Organic Chemistry 36, 3843, 1971).

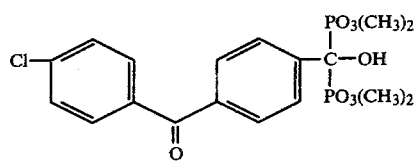

The starting compound 4(4'-chlorobenzoyl)-benzoyl chloride was prepared according to G. E. Robinson and J. M. Vernon, Journal of Chemical Society (C), 2586, 1970, and to E. Wertheim, Journal of American Chemical Society 55, 2540, 1933.

Trimethyl phosphite (10.9 g, 88 mmol, 10% excess) was added dropwise to the acid chloride (22.4 g, 80 mmol) heated to just below the melting point (about 100°). The reaction was exothermic and the white crystals of acid chloride turned into a brown oil with considerable foaming. The reaction mixture was stirred at 100° C. for thirty minutes. Upon standing and cooling the oily material was transformed into an orange solid. Recrystallization in a 60:40 chloroform:petroleum ether mixture gave 20 g (56.7 mmol) of pure dimethyl 4(4'-chlorobenzoyl)benzoylphosphonate.

| mp | = 95-97° (yellow powder) | |
|---|---|---|
| yield | = 71% | |
| IR (KBr) | 2960 cm$^{-1}$ | : aliphatic C—H |
| | 1665 + 1650 | : C=O (pertaining to the benzoylphosphonate and benzophenone moieties) |
| | 1590 | : aromatic C—C |
| | 1250 + 1260 | : P=O |
| | 1050 + 1030 | : P—O—C |

Then a mixture of 2.20 g (20 mmol) of dimethyl phosphite and 0.144 g (1.10 mmol) di(n-butyl) amine in 40 ml ether was cooled to 0° C., and a filtered solution of 7.04 g (20 mmol) of dimethyl 4(4'-chlorobenzoyl) benzoylphosphonate on 40 ml dichloromethane was introduced dropwise. A white precipitate soon separated out of the yellow mother liquor. The reaction mixture was stirred for one hour at 0° C. and the precipitate was filtered and washed by ether. Recrystallization in acetone gave white crystals (2.4 g, 5.2 mmol) of tetramethyl-1[4(4'-chlorobenzoyl)phenyl]methane 1-hydroxy 1,1-diphosphonate.

| mp | = 150-153° C. | |
|---|---|---|
| yield | = 26% | |
| IR (KBr) | : 3280 cm$^{-1}$ | : OH |
| | 1670 | : C=O |
| | 1600 | : aromatic C—C |
| | 1260 + 1240 | : P=O |
| | 1050 + 1030 | : P—O—C |

MS (m/e):

464 (M+2)$^+$: 14%

462 (M)$^+$: 42%

355 (M+2-PO$_3$Me$_2$)$^+$: 32%

353 (M-PO$_3$Me$_2$)$^+$: 100%

NMR (CDCl$_3$):

= 8.10–7.30 (multiplet, 8H): H from the two phenyl groups.

4.5–4.3 (triplet, 1H, J=7 Hz): H from hydroxyl group, removed through exchange with D$_2$O.

3.95–3.60 (multiplet, 12H): H from the methyl groups.

EXAMPLE 4

Dimethyl [1(dimethoxyphosphinyl) p-chlorobenzyl]phosphate (Compound 9)

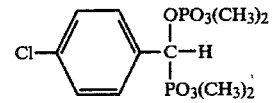

Dimethyl p-chlorobenzoylphosphonate (9.96 g, 40 mmol) was introduced dropwise into a solution of equimolar amounts of dimethyl phosphite (4.40 g, 40 mmol) and di(n-butyl) amine (5.17 g, 40 mmol) that was cooled to 0° C. prior to the addition. A white solid began to form almost immediately. After stirring for one hour at 0° C., the solid was separated by filtration. Recrystallization performed at room temperature in a 1:3 dichloromethane: ether mixture gave 12.0 g (33 mmol) of white crystals.

| mp | = | 81–82° | |
|---|---|---|---|
| yield | = | 82% | |
| IR (KBr) | = | 2980 cm$^{-1}$ | : aliphatic C—H |
| | | 1500 | : aromatic C—C |
| | | 1290 + 1260 | : P=O |
| | | 1050 | : P—O—C |

NMR (CDCl$_3$):
$\delta$ = 7.5–7.3 (multiplet, 4H): phenyl group.
5.85–5.40 (multiplet, 1H): H from the methylene group (non removable through exchange with deuterium oxide).
3.95–3.50 (multiplet, 12H): H from the methyl groups.
Elementary analysis: C$_{11}$H$_{17}$ClO$_7$P$_2$; Calculated: C 36.84 H 4.78 P 17.27%; Found: C 36.71 H 4.86 P 17.33%.

EXAMPLE 5

Tetraethyl 4-phenylbutylidene 1,1-diphosphonate (Compound 16)

(Method adapted from H. R. Hays and T. J. Logan, Journal of Organic Chemistry 31, 3391, 1966, and from O. T. Quimby et al, Journal of Organometallic Chemistry 13, 199, 1968).

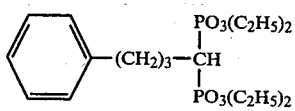

Tetraethyl methylenediphosphonate (23.06 g, 80 mmol) prepared according to Monatshefte Chemie 81, 202, 1950 was added dropwise to a dispersion of sodium hydride (1.92 g, 80 mmol) in 30 ml toluene. When the evolution of hydrogen ceased, 3-phenylpropyl bromide (19.9 g, 100 mmol) was added and the mixture was heated to 90° C. for 14 hours and then to 110° C. for 2 more hours. After removal of the toluene under vacuum, the residue was dissolved in chloroform, washed repeatedly with a saturated sodium chloride solution and freed of water by passing through a silicone-treated filter. Distillation under reduced pressure gave a colorless oil boiling at 135°–145°/5.10$^{-2}$ Torr. A careful refractionation yielded 10.4 g (26 mmol) of tetraethyl 4 phenyl-butylidene 1,1-diphosphonate.
bp = 141°–143°/5.10$^{-2}$ Torr.
yield = 32%.
IR (KBr): see Table II.
MS (m/e):
406 (M)$^+$ 61%
301 100%
269 (M—PO$_3$Et$_2$) 23%.
NMR (CDCl$_3$):
$\delta$ = 7.35–7.2: (multiplet, 5H): phenyl group.
4.45–3.90: (quintet, 8H, J = 8 Hz) H from the four methylene groups attached to the phosphonate moieties.
2.80–1.70: (multiplet, 7H): H from the odd hydrogen and from the side-chain methylene groups.
1.50–1.20: (triplet, 12H, J = 7 Hz): H from the four methyl groups.

EXAMPLE 6

4-Phenylbutylidene 1,1-diphosphonic acid (Compound 19)

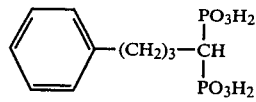

A mixture of 8.15 g (20 mmol) of tetraethyl 4-phenylbutylidene 1,1-diphosphonate and 40 g of 37% hydrochloric acid was refluxed for 15 hours. Evaporation to dryness of the clear acid solution gave a white sticky solid. The compound was repeatedly triturated with ether to remove its stickiness. Recrystallization from an ether:acetone:hexane (30:40:30) mixture gave 3.8 g (13 mmol) of white powder.
mp = 190°–192° C.
yield = 65%.
IR (KBr): see Table III.

EXAMPLE 7

Tetramethyl 4-phenylbutylidene 1,1-diphosphonate (Compound 22)

(Method adapted from D. A. Nicholson et al., Journal of Organic Chemistry 35, 3149, 1970).

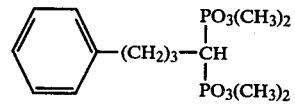

A suspension of 4.5 g (15 mmol) of 4-phenylbutylidene 1,1-diphosphonic acid and 9.8 g (92 mmol) of trimethyl orthoformate was heated to reflux for ninety minutes. Rapid stirring was necessary to assure intimate contact of the two phases. An excess of trimethyl orthoformate (9.8 g, 92 mmol) was then added and the mixture was refluxed for a further thirty minutes. The methanol and methyl formate that were formed were removed by distillation thereby allowing the reaction temperature to rise. Heating was continued until one phase remained and trimethyl orthoformate began to distill. After removal of this reagent, the brown residue was submitted to vacuum distillation to give 3.3 g (9.3 mmol) of a colorless oil.
bp = 135°–138° (5.10$^{-2}$ mmHg).
yield = 62%.
IR (film): see Table III
NMR (CDCl$_3$):
$\delta$ = 7.35–7.20 (multiplet, 5H): phenyl group.
3.95–3.60 (doublet, 12H, J = 11 Hz): H from the methyl groups attached to the phosphonate moieties.
2.80–1.60 (multiplet, 7H): H from the odd hydrogen and from the sidechain methylene groups.

Other compounds of formula (I) were prepared according to similar processes as above, and the physical properties of the compounds (I) prepared are shown on the following Tables I, II and III. NMR spectra of the hydroxy diphosphonate compounds (Ia) (Compounds 1 to 6) all displayed the characteristic absorptions of a hydroxy group: a broad hump (for compounds 1 and 5), or a triplet (compounds 2, 3, 4 and 6), that all were removed through exchange with deuterium oxide.

The NMR spectra of phosphonophosphate compounds (Ib) also displayed a characteristic pattern:
δ≃7.4–7.3 multiplet, phenyl group.
δ=5.8–5.4 (Compounds 9 and 10).
5.2–4.8 (Compounds 11 and 12). multiplet corresponding to the absorption of the odd hydrogen atom, non removable through exchange with deuterium oxide
δ≃3.9–3.5 multiplet, methyl ester groups.
δ=1.55 (only for compounds 11 and 12) singlet, branched methyl group

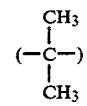

The MS spectra of all diphosphonate ester compounds (Ia and Ic) showed a characteristic pattern: a molecular ion (M+) in significant intensity (30–50%) and a base peak (100%) corresponding to the loss of a phosphonate ester group $(M-PO_3R_2)^+$.

The sole exception is the mass spectrum of compound 5 which did not show the molecular ion but peaks corresponding to the breakdown of the molecule. The structure of the compound was established without ambiguity by micro-analysis.

TABLE I

Physical properties of hydroxydiphosphonates of formula (Ia)

| Compound No. | Formula (Ia) A | R,R' | mp (°C.) | IR absorptions (cm$^{-1}$) |
|---|---|---|---|---|
| 1 | (CH$_3$)$_3$C— | CH$_3$ | 110–112 | 3250 : OH |
|   |   |   |   | 2980 aliphatic C—H |
| 2 | C$_6$H$_5$— | CH$_3$ | 129–131 |   |
|   |   |   |   | 1260 + 1240 : P = O |
| 3 | H$_3$C—C$_6$H$_4$— | CH$_3$ | 110–113 |   |
| 4 | Cl—C$_6$H$_4$— | CH$_3$ | 119–123 | 1050 : P—O—C |
| 5 | Cl—C$_6$H$_4$—O—C(CH$_3$)$_3$ | CH$_3$ | 137–138 | 3340, 1500, 1260, 1240, 1070 |
| 6 | Cl—C$_6$H$_4$—CO—C$_6$H$_4$— | CH$_3$ | 150–153 | 3280, 1670 (C=O) |
|   |   |   |   | 1600, 1260 + 1240 |
|   |   |   |   | 1050 + 1030 |
| 7 | C$_6$H$_5$— | ¾ H ¼ Na | >300 |   |
|   |   |   |   | 3000 (broad) P—O—H— |
|   |   |   |   | 1200–1080–950 |
| 8 | Cl—C$_6$H$_4$— | ¾ H ¼ Na | >300 |   |

TABLE II

Physical properties of phosphonophosphates of formula (Ib)

| Compound No. | Formula (Ib) A | R,R' | mp (°C.) | IR absorption (cm$^{-1}$) |
|---|---|---|---|---|
| 9 | Cl—C$_6$H$_4$— | CH$_3$ | 81–82 | 2980 : aliphatic C—H |
|   |   |   |   | 1500 : aromatic C—C |
| 10 | C$_6$H$_5$— | CH$_3$ | 152–155* | 1290 + 1260 : P=O |
|   |   |   |   | 1050 : P—O—C |
| 11 | C$_6$H$_5$—C(CH$_3$)$_2$— | CH$_3$ | 47–48 | 2980 : aliphatic C—C |
|   |   |   |   | 1500 : aromatic C—C |
|   |   |   |   | 1280 + 1260 : P=O |

TABLE II-continued

Physical properties of phosphonophosphates of formula (Ib)

| Compound No. | Formula (Ib) A | R,R' | mp (°C.) | IR absorption (cm$^{-1}$) |
|---|---|---|---|---|
| 12** | Cl—C$_6$H$_4$—C(CH$_3$)$_2$— | CH$_3$ | 62–63 | 1200 + 1180 : —C(CH$_3$)$_2$— group<br>1050 : P—O—C |

*bp (5.10$^{-2}$ Torr)

**MS Spectra : m/e : 402 (M +: 2)$^+$ : 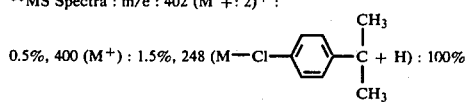
0.5%, 400 (M$^+$) : 1.5%, 248 (M—Cl—C$_6$H$_4$—C(CH$_3$)$_2$ + H) : 100%

TABLE III

Physical properties of diphosphonates of formula (Ic)

| Compound No. | Formula (Ic) A | R,R' | bp (°C./Torr) | mp (°C.) | IR absorptions (cm$^{-1}$) |
|---|---|---|---|---|---|
| 13 | C$_6$H$_5$—CH$_2$— | C$_2$H$_5$ | 135–138/5.10$^{-2}$ | | 2980 : aliphatic C—H |
| 14 | Cl—C$_6$H$_4$—CH$_2$— | C$_2$H$_5$ | 153–156/5.10$^{-2}$ | | 1500 : aromatic C—C |
| 15 | C$_6$H$_5$—(CH$_2$)$_2$— | C$_2$H$_5$ | 137–140/5.10$^{-2}$ | | 1260 : P=O<br>1170 : P—O—C$_2$H$_5$ |
| 16 | C$_6$H$_5$—(CH$_2$)$_3$— | C$_2$H$_5$ | 141–143/5.10$^{-2}$ | | 1050 : P—O—C— |
| 17 | C$_6$H$_5$—CH$_2$— | H | | 210–212 | 3400–3200 (broad):OH<br>1500 : aromatic C—C |
| 18 | Cl—C$_6$H$_4$—CH$_2$— | H | | 237–239 | |
| 19 | C$_6$H$_5$—(CH$_2$)$_3$— | H | | 190–192 | 1040 : P—O— |

Physical properties of diphosphonates of formula (Ic)

| Compound No. | Formula (Ib) R | R' | bp (°C./Torr) | mp (°C.) | Ir absorptions (cm$^{-1}$) |
|---|---|---|---|---|---|
| 20 | C$_6$H$_5$—CH$_2$— | CH$_3$ | 130–132/5.10$^{-2}$ | | 2980 : aliphatic C—H<br>1500 : aromatic C—C |
| 21 | Cl—C$_6$H$_4$—CH$_2$— | CH$_3$ | 141–144/5.10$^{-2}$ | | 1270 : P=O |
| 22 | C$_6$H$_5$—(CH$_2$)$_3$— | CH$_3$ | 135–138/5.10$^{-2}$ | | 1050 : P—O—C |

The present invention will be now further illustrated through the following Examples 8 to 11 concerning the pharmacological activity of the compounds of formula (I).

EXAMPLE 8

Effects of diphosphonates of formula (I) on lipid metabolism in normal rats Method used:

Groups of 4 or 5 normal male Wistar rats, weighing about 200 g were treated with diphosphonates (200 mg/kg/day) p.o. for 4 to 21 days. Water soluble compounds were given in solution in 24 mM bicarbonate buffer. Lipid soluble compounds were given in corn oil. The rats were weighed, sacrified by decapitation (under light ether anesthesia) after overnight fasting. Blood was collected and serum used for analysis. The following blood parameter reflecting changes in lipid metabolism are reported:

free fatty acids measured according to W. G. Duncombe (Clin. Acta 9, 122, 1964).

triglycerides enzymatic method (Boehringer Mannheim Kit 126 012).

phospholipids: molybdate/vanadate reaction (Boehringer Mannheim Kit 124 974).

β-lipoproteins cholesterol was measured after heparin, CaCl$_2$ precipitation according to M. Burstein et al. (La Presse Médicale 43, 974, 1958) and to D. Watson (Clin. Chim. Acta. 5, 637, 1960).

Results obtained:

With the exception of compounds 1, 2 and 3, all the diphosphonates (I) tested lowered serum free fatty acids in normal rats or in cholesterol fed rats. This activity seems to be a rather general property of these diphosphonates which possess a p-chlorophenyl moiety and shows their involvement in lipid metabolism. Similar properties have been described for several hypolipidemic agents ("Hypolipidemic Agents", ed. David Kritchevsky, vol. 41, Handbook of Experimental Pharmacology, Springer-Verlag, 349–408, 1975). Significant decreases in serum triglycerides were measured with compounds, 2, 4, 5, 6, 8 and 14 and the acid form of compound 4. In several cases, compounds 2, 4 5 and 6, serum phospholipid was found to increase. In particular, compound 4 was found to be at least two fold the most active. Cholesterol present in the β-lipoprotein fraction (very low density lipoproteins VLDL, and low density lipoproteins LDL) decreased whereas α-liprotein (high density lipoproteins HDL) cholesterol increased thus leading to a favorable augmentation of the α-cholesterol/β-cholesterol ratio. This effect was associated in long term therapy with a decreased liver and aorta cholesterol content. Clofibrate was tested for comparison purposes and in our hands decreased phospholipids by 33.6% and the α/β ratio decreased by 52.2%. The results are in agreement with those published by C. E. Day et al (Artery 5, 90–109. 1979) and by K. R. Müller and G. G. Cortesi (Artery 4, 564–577, 1978) demonstrating that clofibrate decreases HDL cholesterol in rats.

The results described above show that these diphosphonates have the property to change lipid metabolism especially to increase the amount of lipid (mainly cholesterol) carried by α-lipoproteins and decrease the amount of lipids carried by β-lipoproteins (mainly triglycerides). Since it has been shown that the amount of HDL-cholesterol inversely correlates with the risk of cardiovascular disease (see N. E. Miller, Lipids 13, 914–919, 1978), diphophonates having the property to increase HDL levels might be useful in the portential treatment of atherosclerosis. It is important to note that the acid or salt form of compound 4 and the rather simple diphosphonate compound 1, do no have these properties. It is also important to note that diphosphonates which are structurally different from compounds 2, 4, 5, 6 and tested by others do not have the property to act on lipid metabolism (see W. Hollander et al., Atherosclerosis 31, 307–325, 1978 and Mellies et al., Artery 6, 38, 1979).

EXAMPLE 9

Effects of diphosphonates of formula (I) in cholesterol fed rats

Method used:

In order to increase tissue cholesterol, especially liver, rats were fed a high fat-high cholesterol diet for 10 days to 3 months, with the following diet composition: casein 20%, butter 37%, cellulose 9.1%, dextrose 18.9%, cholesterol 4.5%, sodium cholate 1.8%, minerals 7.3%, vitamins 1%, choline 0.4%.

The rats were then fed normal food and were treated for 10 days to 3 months with different compounds (200 mg/kg/day). Serum parameters described above were measured. Liver and aorta lipids were extracted according to J. Folch et al (J. Biochem. 226, 497, 1957). Total lipids were determined by the sulfophosphovanillic reaction (see N. Zölner and K. Kirsch, Z. Ges. exp. Med. 135, 545, 1962) and cholesterol by the Liebermann-Burchard reaction.

Results obtained:

The diet described above increased liver total lipids, especially triglycerides and cholesterol, 8 to 10 folds. Treatment with compounds 2, 4, 5, 6, 9 and 14 decreased significantly liver total lipids and/or liver cholesterol. The same effect was measured in the aortic tissue. This shows that these particular diphosphonates tested have the property to remove tissue cholesterol. Since it is well established that cholesterol deposition is an important step in the initiation and/or development of atherosclerosis, these compounds might be useful in the prevention or treatment of atherosclerotic lesions, by preventing cholesterol deposition in tissues such as the aorta.

EXAMPLE 10

Effects of acid and salt form of diphosphonates of formula (I) in hypercalceamic rats Method used:

In recent years, diphosphonic acids have been shown to be effective in the hypercalceamic animal model in which they inhibit aorta and kidney calcification (see M. Potokar and M. Schmidt-Dunker, Atherosclerosis 30, 313–320, 1978). They have also been shown to prevent the vitamin D-induced rise in plasma calcium. This activity might be useful for the regression of preestablished atherosclerosis (see I. Y. Rosenblum et al. Atherosclerosis 22, 411–424, 1975). Since diphosphonates have these activities when given as acids or sodium salts the acid form and its monosodium salt counterpart (compound 8) of compound 4 were also tested by using a protocol similar to the one described by Potokar (see above). Briefly, groups of 4 male Wistar rats received acid or salt form of compound 4 as 0.05% solution in drinking water corresponding to about 50 mg/kg/day. The rats were treated with the compounds for 15 days. From the 5th day to the 10th day hypercalceamia was produced by giving to control and treated rats 75000 U vitamin $D_3$/kg/day. Diphosphonate treatment continued from the 10th to the 15th day. The animals were then sacrified under light ether anesthesia and serum calcium determined according to B.C. Ray Sarkar and U.P.S. Chanhan (Anal. Biochem. 20, 155, 1967).

Results obtained:

Calcium deposition has been considered to play a role in the late stages of the development of atherosclerotic plaques (see W. Hollander, Exp. Mol. Path. 25, 106, 1976), and it has been shown that some diphosphonate acids or salts act on calcium metabolism and that this property by itself might be useful in the treatment of the late stages of atherosclerosis. The fact that none of the esterified forms but the acid and salt forms of compound 4 decrease serum calcium by 20 and 14% respectively indicates that the non-esterified diphosphonates act on calcium metabolism and might decrease calcification of atheromas.

Some results of the above described pharmacological activity tests of diphosphonates of formula (I) according to the present invention are shown in the following Table IV.

TABLE IV

Pharmacological activity of diphosphonates of formula (I)

| Compounds No. | Serum Free Fatty Acids | | Serum Triglycerides | | Serum Phospholipids | | Serum Cholesterol α/β | Liver Tot. Lipids | Liver Cholesterol | Aorta Tot. Lipids | Aorta Cholesterol | Serum Calcium |
|---|---|---|---|---|---|---|---|---|---|---|---|---|
| | N | C.F | N | C.F | N | C.F | C.F | C.F | C.F | C.F | C.F | |
| 2 | NS | −56 | −21 | −15 | +25 | NS | +88 | −24 | −50 | −30 | NS | NS |
| 4 | −48 | −67 | −24 | −21 | +43 | +21 | +220 | −31 | −56 | −47 | NS | NS |
| 5 | +28 | −40 | −33 | NS | +26 | NS | +27 | NS | −25 | −27 | −19 | NS |
| 6 | −38 | −52 | −16 | −17 | NS | +36 | +51 | −25 | NS | NS | −39 | NS |
| 14 | −44 | −65 | −16 | −24 | NS | NS | −35 | NS | NS | −60 | NS | NS |
| 3 | NS | | NS | | NS | | NS | — | — | — | — | NS |
| 1 | NS | | +24 | | −43 | | NS | — | — | — | — | NS |
| 21 | −44 | | +36 | | −18 | | NS | — | — | — | — | NS |
| 9 | −50 | | NS | | +26 | | +169 | −32 | −57 | −37 | −30 | NS |
| 8 (Acid) | −17 | | −29 | | NS | | NS | NS | NS | NS | NS | −20 |
| 8 | −27 | | −17 | | NS | | NS | NS | NS | NS | NS | −14 |
| Clofibrate | NS | | +19 | | −34 | | NS | — | NS | — | — | — |

Note:
In above Table IV, results are given as % control values. Except for serum calcium, values which differ from control values by less than 15% are considered as non significant (NS).
Serum free fatty acids, triglycerides and phospholipids were measured in normals rats (N) and in Cholesterol fed rats (C.F.).
Serum α/β cholesterol, total lipids and cholesterol of liver and aorta were determined in rats which had previously been fed a high cholesterol diet.
Serum calcium was measured in hypercalceamic rats.

The pharmacological screening of diphosphonate derivatives of formula (I) according to the present invention has shown that said compounds possess specific properties and activities upon lipids and lipid metabolism, and that they have the potential of being used in the treatment of cardiovascular disease for the following reasons:

They act on lipid metabolism in normal rats by decreasing serum free fatty acids, decreasing triglycerides and increasing phospholipids. The later might be linked to the increased HDL lipids, especially HDL cholesterol, observed most dramatically with compounds 2, 4 and 9.

They possess the important property of decreasing and removing significantly liver and aorta lipids, especially cholesterol, in high fat high cholesterol fed rats. Experiments not reported here have also shown that compounds such as 2 and 4 increase bile and fecal cholesterol excretion leading to a net loss of tissue cholesterol.

It should be thus noted that the primary actions of said diphosphonates (I) are different and novel in comparison to the classical hypolipidemic compounds. The specificity of these activities (increased HDL and tissue clearance of cholesterol) strongly suggest a potential pharmaceutical use in atherosclerosis. Experiments done on rabbits in which experimental atheroselerosis had been induced by cholesterol feeding confirmed the previous observations, that compound 4 which has the p-Cl moiety is the most active.

In addition, the fact that the acid and salt forms of compound 4 act on calcium metabolism suggests that all the non-esterified forms of these diphosphonates described have the potential of being used also to treat the late stages of atherosclerosis.

EXAMPLE 11

Hypoglycemic activity of diphosphonates of formula (I)

Male Wistar rats (5/group) weighing between 150–200 g were treated for 4 days with prescreened phosphonates. They were fasted overnight and sacrified the 5th day by decapitation under light ether anesthesia. Blood sample were collected using EDTA as anticoagulant. Results are given as mean values±sem. The results as seen in Table V indicate that the p-chloro-phenyl diphosphonate was most potent and especially when given i.p.

TABLE V

HYPOGLYCEMIC ACTIVITY

| Route of administration dosage, and vehicle | Controls | Plasma glucose (mg/100 ml) Treated | |
|---|---|---|---|
| | | Cpd 4 | Cpd 2 |
| i.p. 50 mg/kg aq. buffer | 87 ± 3 | 36 ± 1 | |
| p.o. 50 mg/kg aq. buffer | 132 ± 8 | 100 ± 12 | |
| p.o. 50 mg/kg corn oil | 125 ± 10 | 90 ± 5 | |
| p.o. 100 mg/kg aq. buffer | 111 ± 7 | 93 ± 12 | |
| p.o. 50 mg/kg corn oil | 125 ± 10 | | 110 ± 10 |

Glucose concentration was determined by the enzymatic method of W. Werner and H. G. Wielinger (Z. Analyt. Chem. 252, 224, 1970) (obtained from Boehringer Mannheim, No. 124036).

The present invention further includes in its scope hypoglycemic and antiatherogenic preparations, which comprise as active ingredient a pharmaceutically effective amount of one or more diphosphonate derivatives of formula (I).

Safe and effective amounts of phosphonate compound are prepared in sufficient amounts to produce a desirable effect at a reasonable benefit/risk ratio attendant with any medical treatment. Within the scope of acceptable and sound medical judgment, the dosage of phosphonate compound will vary with the particular condition being treated, the severity of the condition, the duration of the treatment, and the specific phosphonate compound employed.

The phosphonates are prepared as pharmaceutically acceptable products which include all ingredients used in the compositions employed and are suitable for use in contact with the tissues of humans and animals without undue toxicity, irritation, allergic response commensurate with a reasonable benefit/risk ratio.

Preparation of the pharmaceutical compositions according to the present invention for oral unit dosage forms can be a mixture with a solid vehicle containing lactose, saccharose, sorbitol, mannitol, starch, amylopectine, cellulose derivative, andor gelatine which can be prepared with the lubricants such as magnesium stearate, calcium stearate, forms of "carbowax" and/or polyethylene glycol. It can be preferable in some cases to use a capsule, and the ingredients can then consist of a mixture containing concentrated sugar, arabic gum, talc, and/or titan bioxide.

Im some cases particular phosphonates can be mixed in buffer solution, corn oil, olive oil, glycerol commercial fillers, and administered in a closed hard gelatin capsule, as drops, or syrup forms.

In addition, the phosphonates can be fabricated with "Imhausen H" to produce suitable suppositories.

For example, compounds 4 to 9 were compressed in tablet form with magnesium stearate 10% and starch 25% to obtain a final concentration of about 100 to 300 mg active agent. In addition compounds of formula (I) were used up in solution of drinking water or corn oil at concentrations between about 2 mg/ml and 100 mg/ml.

We claim:

1. Diphosphonate methyl esters represented by general formula (I)

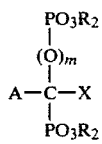

where X is H or OH, R is CH$_3$, m is zero or 1, and A is selected from the group comprising

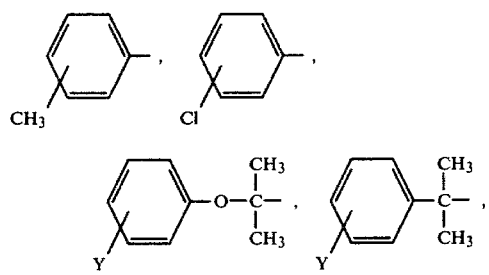

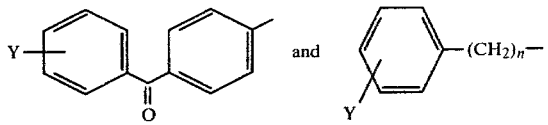

where n is integer from 1 to 6 and Y is H, CH$_3$ or Cl.

2. Hydroxydiphosphonate methyl esters of formula (Ia) according to claim 1,

where R, and A are as defined in claim 1.

3. Phosphonophosphate methyl esters of formula (Ib) according to claim 1,

where R, and A are as defined in claim 1.

4. Diphosphonate methyl esters of formula (Ic) according to claim 1

where R, and A are as defined in claim 1.

5. Tetramethyl 1(p-chlorophenyl)methane 1-hydroxy 1-1-diphosphonate according to claim 1.

6. Tetramethyl 2,2-dimethyl 2-(p-chlorophenoxy)ethane 1-hydroxy-1,1-diphosphonate according to claim 1.

7. Tetramethyl 1-[4(4'-chlorobenzoyl)phenyl]-methane 1-hydroxy 1,1-diphosphonate according to claim 1.

8. Dimethyl 1[(dimethoxyphosphinyl)p-chlorobenzyl]phosphate according to claim 1.

9. Dimethyl [1(dimethoxyphosphinyl) 2,2-dimethyl 2-phenyl]-ethyl phosphate according to claim 1.

10. Dimethyl [1(dimethoxyphosphinyl)2,2-dimethyl 2(p-chlorophenyl] ethyl phosphate according to claim 1.

11. Tetramethyl 4-phenylbutylidene, 1,1-diphosphonate according to claim 1.

* * * * *